United States Patent
Schena (10) Patent No.: US 6,913,879 B1
(45) Date of Patent: Jul. 5, 2005

(54) MICROARRAY METHOD OF GENOTYPING MULTIPLE SAMPLES AT MULTIPLE LOCI

(75) Inventor: Mark A. Schena, Los Altos, CA (US)

(73) Assignee: TeleChem International Inc., Sunnyvale, CA (US)

( * ) Notice: Subject to any disclaimer, the term of this patent is extended or adjusted under 35 U.S.C. 154(b) by 1 day.

(21) Appl. No.: 09/613,006

(22) Filed: Jul. 10, 2000

(51) Int. Cl.[7] .......................... C12Q 1/68; C12P 19/34; C12M 1/36; C07H 21/04
(52) U.S. Cl. .................... 435/6; 435/91.1; 435/91.2; 435/287.2; 536/23.1; 536/24.3; 536/24.31; 536/24.33
(58) Field of Search .................... 435/6, 287.2, 91.1, 435/91.2; 536/24.3, 23.1, 24.31, 24.33, 24.32

(56) References Cited

U.S. PATENT DOCUMENTS

| | | | |
|---|---|---|---|
| 4,981,783 A | 1/1991 | Augenlicht | 435/6 |
| 5,143,854 A | 9/1992 | Pirrung et al. | 436/518 |
| 5,202,231 A | 4/1993 | Drmanac et al. | 435/6 |
| 5,403,708 A | 4/1995 | Brennan et al. | 435/6 |
| 5,445,934 A | 8/1995 | Fodor et al. | |
| 5,545,531 A | 8/1996 | Rava et al. | 435/6 |
| 5,665,540 A | 9/1997 | Lebo | 435/6 |
| 5,700,637 A | 12/1997 | Southern | 435/6 |
| 5,800,992 A * | 9/1998 | Fodor | 435/6 |
| 5,807,522 A | 9/1998 | Brown et al. | 422/50 |
| 5,830,645 A | 11/1998 | Pinkel et al. | 435/6 |
| 5,834,181 A | 11/1998 | Shuber | |
| 5,858,659 A | 1/1999 | Sapolsky et al. | 435/6 |
| 5,919,626 A | 7/1999 | Shi et al. | |
| 5,925,525 A | 7/1999 | Fodor et al. | 435/6 |
| 5,958,342 A | 9/1999 | Gamble et al. | 422/100 |
| 6,013,449 A | 1/2000 | Hacia et al. | 435/6 |
| 6,025,136 A | 2/2000 | Drmanac | 435/6 |
| 6,040,138 A | 3/2000 | Lockhart et al. | 435/6 |
| 6,045,996 A | 4/2000 | Cronin et al. | 435/6 |
| 6,057,100 A | 5/2000 | Heyneker | 435/6 |
| 6,232,066 B1 | 5/2001 | Felder et al. | |
| 6,238,869 B1 | 5/2001 | Kris et al. | |
| 6,268,147 B1 * | 7/2001 | Beattie et al. | 435/6 |
| 2002/0001801 A1 * | 1/2002 | Fan et al. | 435/6 |

FOREIGN PATENT DOCUMENTS

WO    WO 00/18960    4/2000

OTHER PUBLICATIONS

Lashkari et al. "Yeat microarrays for genome wide parallel genetic and gene expression analysis" Proc. Natl. Acad. Sci. USA, 1997, 94: 13057–13062.*

Wang et al. "Large–scale identification, mapping, and genotyping of single–nucleotide polymorphisms in the human genome" Science, 1998, 280: 1077–1082.*

Cheng et al. "A multilocus genotyping assay fro cardiovascular disease" Clin. Chem.Lab. Med.,, 1998, 36(8): 561–566.*

Pease et al. "Light–generated oligonucleotide arrays for rapid DNa sequence analysis" Proc. Natl. Acad. Sci. USA, 1994, 91: 5022–5026.*

(Continued)

*Primary Examiner*—BJ Forman
(74) *Attorney, Agent, or Firm*—Morrison & Foerster LLP (57) ABSTRACT

A method for genotyping multiple samples at multiple genetic loci in a single assay is provided. Microarrays of genomic segments representing discrete loci are formed and hybridized with mixtures of synthetic oligonucleotides that are complementary to the genomic segments. Genotyping information is derived by reading the microarray signals. The method can be used to characterize samples from diverse biological sources and for a variety of applications.

19 Claims, 5 Drawing Sheets

OTHER PUBLICATIONS

Morris, C. Academic Press Dictionary of Science and Technology, Adademic Press, 1992, p. 2157.*

Nucleic Acid Hybridization: a practical approach, IRL Press, Washington DC, 1985, pp. 105–108.*

Skogerboe, K. J. et al. (1990). "Development and Evaluation of a Simplified Dot–Blot Method for Detecting the Delta–F508 Mutation in Cystic Fibrosis," *Clinical Chemistry* 36(11):1984–1986.

Wang, B. T. et al. (1998). "Molecular and Biochemincal Basis of Galactosemia," *Molecular Genetics and Metabolism* 63(4):263–269.

Giles, et al., "Single nucleotide Polymorphic discrimination by an electronic dot blot assay on semiconductor microchips", Nature Biotechnology, vol. 7, pp. 365–369 (Apr. 1999).

Kononen, et al., "Tissue microarrays for high–throughput molecular profiling of tumor specimens", Nature Medicine, vol. 4, No. 7, pp. 844–847 (Jul. 1998).

http://arrayit.com/biochip4/, "ArrayIt™ Stealth Micro Spotting Technology", 5 pages, Jul. 6, 2000.

http://arrayit.com/microarray–substrates. ArrayIt™ Super Microarray Substrates Handbook, 9 pages, Jul. 6, 2000.

http://www.polygenyx.com/technology.html, PolyGenyx, Inc. Technology & Applications, 14 pages, Jul. 6, 2000.

Dobrowolski, S.F. et al., (1999) "DNA microarray technology for neonatal screening" *Acta Paediatr Suppl.* 432:61–64.

Item, C. et al., (2002) "Mutations at the galactose–1–P–uridyltransferase gene in infants with a positive galactosemia newborn screening test" *Pediatric Research* 51(4):511–516.

Schena, M. et al., (Oct. 20, 1995) "Quantitative monitoring of gene expression patterns with a complementary DNA microarray" *Science* 270:467–470.

Schena, M. (1996) "Genome analysis with gene expression microarrays" *BioEssays* 18(5):427–431.

Schena, M. et al., (Oct. 1996) "Parallel human genome analysis: microarray–based expression monitoring of 1000 genes" *Proc. Natl. Acad. Sci., USA, Biochemistry* 93:10614–10619.

Schena, M. et al., (Jul. 1998) "Microarrays: biotechnology's discovery platform for functional genomics" *TIBTECH* 16:301–306.

zielenski, J. et al., (1991) "Genomic DNA sequence of the cystic fibrosis transmembrane conductance regulator (CFTR) gene" *Genomics* 10:214–228.

* cited by examiner

SEQUENCE LISTING

```
<160> NUMBER OF SEQ ID NOS: 30

<210> SEQ ID NO 1
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = adenine with C6 modification

<400> SEQUENCE: 1
naacagacac catggtgcac                                                 20

<210> SEQ ID NO 2
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine with a C6 modification

<400> SEQUENCE: 2
nccacagggc agtaacggca                                                 20

<210> SEQ ID NO 3
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = guanine with a C6 modification

<400> SEQUENCE: 3
ncaaggtgaa cgtggatgaa                                                 20

<210> SEQ ID NO 4
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = guanine with a C6 modification

<400> SEQUENCE: 4
ntaaccttga taccaacctg                                                 20

<210> SEQ ID NO 5
<211> LENGTH: 20
<212> TYPE: DNA
<213> ORGANISM: Homo sapiens
<220> FEATURE:
<221> NAME/KEY: misc_feature
```

```
<222> LOCATION: 1
<223> OTHER INFORMATION: n = cytosine with a C6 modification

<400> SEQUENCE: 5
ntggcaccat taaagaaaat                                                     20

<210> SEQ ID NO 6
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = thymine with a C6 modification

<400> SEQUENCE: 6
ntctgtatct atattcatca                                                     20

<210> SEQ ID NO 7
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = thymine with a C6 modification

<400> SEQUENCE: 7
ngggctgttc taaccccac                                                      20

<210> SEQ ID NO 8
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = adenine with a C6 modification

<400> SEQUENCE: 8
nacccactgg agcccctgac                                                     20

<210> SEQ ID NO 9
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine with a C6 modification

<400> SEQUENCE: 9
ncacaggatc agaggctggg                                                     20

<210> SEQ ID NO 10
<211> LENGTH: 20
<212> TYPE: DNA
<213> ORGANISM: Homo sapiens
<220> FEATURE:
<221> NAME/KEY: misc_feature
<222> LOCATION: 1
<223> OTHER INFORMATION: n = guanine with a C6 modification

<400> SEQUENCE: 10
ngtagtaatg agcgtgcagc                                                     20

<210> SEQ ID NO 11
```

```
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = guanine with a Cy3 label
<220> FEATURE:
<221> NAME/KEY: variation
<222> LOCATION: 9
<223> OTHER INFORMATION: n = a or t

<400> SEQUENCE: 11
nactcctgng gagaa                                               15

<210> SEQ ID NO 12
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = guanine with Cy5 labels
<220> FEATURE:
<221> NAME/KEY: variation
<222> LOCATION: 9
<223> OTHER INFORMATION: n = a or t

<400> SEQUENCE: 12
nactcctang gagaa                                               15

<210> SEQ ID NO 13
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = thymine attached to a Cy5 label

<400> SEQUENCE: 13
nggtggtgag gccct                                               15

<210> SEQ ID NO 14
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = thymine attached to a Cy3 label

<400> SEQUENCE: 14
nggtggtaag gccct                                               15

<210> SEQ ID NO 15
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = adenine attached to Cy3

<400> SEQUENCE: 15
ntcatctttg gtgtt                                               15

<210> SEQ ID NO 16
<211> LENGTH: 15
```

```
<212> TYPE: DNA
<213> ORGANISM: Homo sapiens
<220> FEATURE:
<221> NAME/KEY: misc_feature
<222> LOCATION: 1
<223> OTHER INFORMATION: n = thymine attached to a Cy5 label

<400> SEQUENCE: 16
natcatcggt gtttc                                                      15

<210> SEQ ID NO 17
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to a Cy5 label

<400> SEQUENCE: 17
nactgccagg taagg                                                      15

<210> SEQ ID NO 18
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to a Cy3 label

<400> SEQUENCE: 18
nactgccggg taagg                                                      15

<210> SEQ ID NO 19
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to a Cy3 label

<400> SEQUENCE: 19
naactggaac cattg                                                      15

<210> SEQ ID NO 20
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to a Cy5 label

<400> SEQUENCE: 20
naactgggac cattg                                                      15

<210> SEQ ID NO 21
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = guanine attached to biotin
<220> FEATURE:
<221> NAME/KEY: variation
<222> LOCATION: 9
```

```
<223> OTHER INFORMATION: n = a or t

<400> SEQUENCE: 21
nactcctgng gagaa                                              15

<210> SEQ ID NO 22
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = thymine attached to  biotin

<400> SEQUENCE: 22
nggtggtaag gccct                                              15

<210> SEQ ID NO 23
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = adenine attached to biotin

<400> SEQUENCE: 23
ntcatctttg gtgtt                                              15

<210> SEQ ID NO 24
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to biotin

<400> SEQUENCE: 24
nactgccggg taagg                                              15

<210> SEQ ID NO 25
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached biotin

<400> SEQUENCE: 25
naactggaac cattg                                              15

<210> SEQ ID NO 26
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = guanine attached to dinitrophenol
<220> FEATURE:
<221> NAME/KEY: variation
<222> LOCATION: 9
<223> OTHER INFORMATION: n = a or t

<400> SEQUENCE: 26
nactcctang gagaa                                              15
```

```
<210> SEQ ID NO 27
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = thymine attached dinitrophenol

<400> SEQUENCE: 27
nggtggtgag gccct                                                    15

<210> SEQ ID NO 28
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = thymine attached to dinitrophenol

<400> SEQUENCE: 28
natcatcggt gtttc                                                    15

<210> SEQ ID NO 29
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to dinitrophenol

<400> SEQUENCE: 29
nactgccagg taagg                                                    15

<210> SEQ ID NO 30
<211> LENGTH: 15
<212> TYPE: DNA
<213> ORGANISM: Homo sapiens
<220> FEATURE:
<221> NAME/KEY: misc_feature
<222> LOCATION: 1
<223> OTHER INFORMATION: n = cytosine attached to dinitrophenol

<400> SEQUENCE: 30
naactgggac cattg                                                    15
```

MICROARRAY METHOD OF GENOTYPING MULTIPLE SAMPLES AT MULTIPLE LOCI

TECHNICAL FIELD

The present invention relates generally to genotyping and more particularly to genotyping for disease diagnostics.

BACKGROUND

A large number of pathological conditions in humans, animals, and plants are now understood at the genetic level. With the announced completion of the mapping of the human genome, it is expected that the genetic basis of many more human diseases will be identified in the coming years. Analysis of DNA from an individual, therefore, can, in principle, allow genetically based conditions to be diagnosed or to be identified in the absence of overt symptoms. This is advantageous for many conditions such as metabolic disorders in which early diagnosis can prevent serious medical complications later in life.

Methods of analyzing DNA sequences, which are often referred to generically as genotyping, are known in the art. In very general terms, to determine whether the DNA in a sample corresponds to a particular disease condition whose genetic sequence is known, the sample is exposed to nucleic acid probes associated with that disease, under conditions that allow hybridization. The nucleic acid probes are labeled making it possible to detect whether the probes have hybridized to the DNA sample. In one technique, the probes are arranged in arrays on chips, with each probe assigned to a specific location. After exposing the array to a labeled DNA sample, scanning devices can examine each location in the array and determine whether a target molecule has interacted with the probe at that location. Array chips are provided commercially, for example, by Affymetrix (Santa Clara, Calif.) and are described in patents assigned to Affymetrix (See, for example U.S. Pat. Nos. 6,045,996, 5,858,659, and 5,925, 525, and references therein.). Arrays have also been used for DNA sequencing applications such as the Sequencing by Hybridization approaches described, for example, in U.S. Pat. Nos. 6,025,136, 6,018,041, 5,525,464, and 5,202,231.

While methods of genotyping for disease diagnostics are available, in order for the methods to be useful in a public health setting, they need to be reasonable in cost. For example, although relevant genetic assays are known, neonatal screening is currently done by mass spectrometric methods primarily because of cost considerations. Secondly, DNA diagnostics in a public health setting need to be practical for application to multiple samples and to genetic conditions in which mass spectrometric methods are difficult or intractable. The requirement of multiple samples may be addressed by using multiple array chips, which are processed simultaneously. As described in U.S. Pat. No. 5,545, 531 to Rava et al., a format including a standard 96-well microtiter plate containing an array chip at the bottom of each well can be used. To perform the same test on many patient samples, each patient sample, in solution, is labeled and introduced into a different well, each of which has an identical array chip. Thus, in this method, a separate array chip is used for each sample, which may be costly for widespread use because of the fixed per-patient costs of arrays, reagents, sample processing, and so forth.

U.S. Pat. No. 5,807,522 to Brown et al. describes a method of screening multiple patients against known mutations in a disease gene using multiple microarrays of patient genomic DNA and probe DNA fragments representing all known mutations of a given gene. The microarrays are fabricated on a sheet of plastic-backed nitrocellulose with silicone rubber barrier elements between individual arrays to prevent cross contamination. All microarrays are processed as a single sheet of material. However, the method of Brown et al. uses a separate microarray for each mutated allele or genetic marker screened.

Thus, there is a need for a method of genotyping with sufficient precision for diagnostic use, that is affordable and that provides sufficient throughput for large-scale use. Ideally, such a method would allow multiple patients to be screened for multiple diseases in a single assay. More generally, the method would allow multiple samples from any source of human, animal, plant, or microbial material to be screened for alleles at multiple genetic loci in a single assay.

SUMMARY

The present invention provides a method for genotyping multiple samples at multiple genetic loci in a single assay. According to the method, genomic segments from multiple samples are amplified using polymerase chain reaction primers, where each genomic segment contains a genetic locus, that is, a DNA marker of interest. The genomic segments are formed into a microarray on a surface where the material at each location of the surface corresponds essentially to a single genomic segment from a single sample. The microarray is hybridized with a mixture of synthetic oligonucleotides that are complementary to the genomic segments on the micorarray. Genotyping information for the multiple samples is then derived simultaneously by reading the microarray signals. The method can be used for disease diagnostics or to screen for alleles from any plant or animal species and thus can be used for a broad variety of applications.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 4A and 4B are magnified portions of the data in FIGS. 3A and 3B, respectively. Letters (a–c) and numbers (1–28) demarcate the location of each of the different patient samples as follows: a10 –12, sample 1 (S/S); a13–15, sample 2 (A/S); a16–18, sample 3 (S/C); a19–21, sample 4 (C/C); a22–24, sample 5 (A/C); a25–27, sample 6 (A/A); b1–3, sample 7 (E/E); b4–6, sample 8 (A/E); b7–9, sample 9 (A/A); b10–12, sample 10 (wild type); b13–15, sample 11

(heterozygous); b16–18, sample 12 (homozygous); b19–21, sample 13 (wild type); b22–24, sample 14 (heterozygous); b25–27, sample 15 (homozygous). Background subtraction was performed using the signal from the negative control printing buffer (a28–30). Positive hybridization controls (b28–30, c1–3, c4–6, c7–9 and c10–12) are also shown. The space bar corresponds to 1.0 mm.

FIG. 5 displays quantitative values of the signals represented by the rainbow code in FIG. 4A. Triplicate measurements were averaged after background subtraction. The genotypes of each patient sample are given above and below the graph.

DETAILED DESCRIPTION

A method of genotyping obtains information about multiple individuals at multiple disease loci simultaneously. As used herein, genotyping is specifically defined as distinguishing alleles at a given genetic locus at single nucleotide resolution. A genetic locus (plural loci) is defined as a chromosomal location of a genetic or DNA marker. Thus the methods according to the present invention have the precision required to provide screening and diagnostic information for individuals that can be used as the basis for medical decisions.

Figure 1:
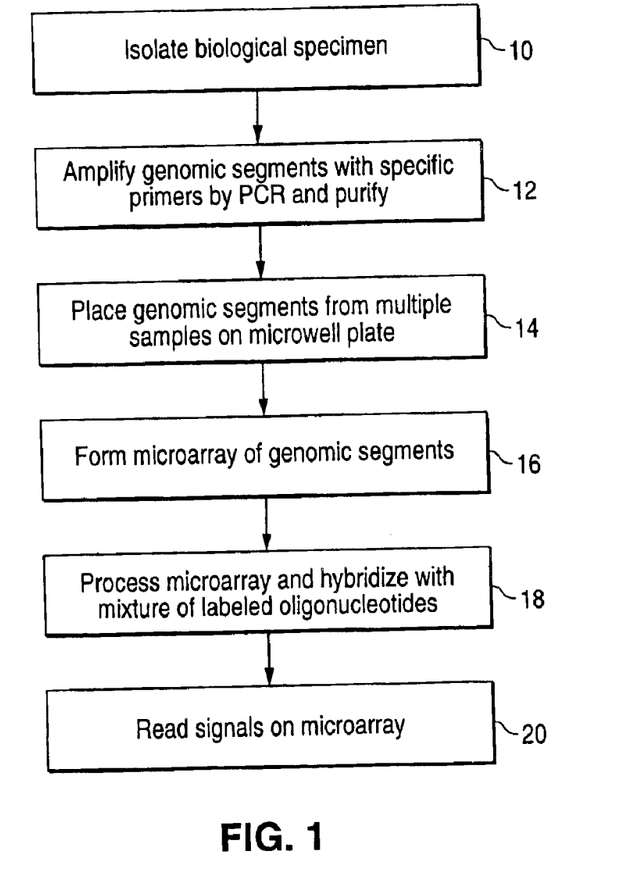
FIG. 1 is a flow chart of a method of genotyping multiple samples at multiple genetic loci simultaneously according to an embodiment of the present invention.

An overview of the method is illustrated diagrammatically in FIG. 1. First, at step 10, samples of genomic DNA are isolated from biological specimens. The specimens can be of any origin including bacteria, yeast, plants or animals. Any organism that contains DNA is amenable to the method. For application to human disease diagnostics, biological specimens are obtained, for example, from blood, amniotic fluids, neonatal blood cards, saliva, semen, epithelial scrapes, and needle biopsies. For certain organisms, the biological specimens may contain RNA but not DNA. The samples are isolated and purified using standard procedures.

Sample DNA is then amplified with gene-specific primers by use of the polymerase chain reaction (PCR) at step 12 to produce the so-called amplicons. The PCR process is broadly used and has been described extensively in the art (see for example, U.S. Pat. Nos. 4,683,202 and 4,683,195 and 4,800,159 and 4,965,188 and 5,333,675 and references therein). A specific pair of primers is used for each genomic segment of interest, that is for each genomic segment containing a known potential mutation or other DNA alteration of interest. The method is applicable, therefore, to any disease identified with DNA markers. Such diseases include, for example Cystic Fibrosis, Tyrosinemia, Maple Syrup Urine Disease, α-1-Antitrypsin Deficiency, Glutaric Aciduria Type 1, Hereditary Hearing Loss, Beta-Thalassemia, Long Chain 3-Hydroxyl Acyl CoA Dehydrogenase Deficiency, Medium Chain Acyl CoA Dehydrogenase Deficiency to name a very few. The method is particularly useful for diseases such as Sickle Cell Anemia and Galactosemia wherein a well-studied single mutation in a single gene can produce the disease phenotype. The DNA markers could represent any of the known types of DNA alterations including mutations, single nucleotide polymorphisms, small deletions and the like. The only requirement is that the DNA alteration of interest must reside within the primer pairs used to generate the amplicons. This ensures that amplicons generated from all of the specimens at a given locus, including specimens from homozygotes, heterozygotes and normal individuals, amplify with nearly equal efficiency.

Each biological sample is treated separately with multiple primer pairs to produce multiple amplicons for each individual, each amplicon associated with a specific genomic segment from a specific individual, each genomic segment containing a genetic locus of interest. The length of each amplicon, as the method is currently practiced is about 60 base pairs, although the method may be applied with amplicons in the range of between about 40 and 1000 base pairs. The total volume of each PCR reaction as is typically practiced currently is about 50 $\mu$l. It is anticipated that further optimization will reduce the minimum volume to 5–10 $\mu$l, which will allow the method to provide additional cost savings by minimizing the amount of the PCR amplification and purification reagents used for sample preparation.

The genomic segments are purified to remove contaminants such as nucleotides, enzyme, primers and other substances that may interfere with microarray printing, attachment or hybridization. Methods for PCR amplicon purification are available from a host of commercial vendors including TeleChem (Sunnyvale, Calif.) and Qiagen (Valencia, Calif.). The purified amplicons are suspended in buffers such as solutions of sodium chloride and sodium citrate (SSC), solutions of dimethyl sulfoxide (DMSO), solutions of sodium chloride, sodium phosphate and ethylene diamine tetraacetate (SSPE) or other standard reagents. The buffered amplicons are arrayed in standard 96-well or 384-well microplates, in step 14, one amplicon solution per well. Typical volumes of purified product are about 3–4 $\mu$l per well for the arraying step, although product volumes in the range of 2–20 $\mu$l are sufficient for forming the microarrays.

The DNA isolation and PCR processes are readily scaleable in either 96-well or 384-well configurations such that >10,000 samples per day are readily achieved in an automated laboratory setting. This throughput would allow amplification of 10 loci from 240,000 patients annually. The method thus enables broad screening of the population as well as other high-throughput applications such as a required for crop breeding in agriculture, forensics, military applications, and the like.

In step 16, a high-density microarray of the genomic segments in the microplate is formed on a substrate, with the current size of the microarray occupying about 1.0 cm$^2$ on the substrate that is typically the size of a standard 25 mm×76 mm microscope slide. A typical spot diameter is about 100 $\mu$m placed at a center-to-center spacing of about 140 $\mu$m, to allow each spot to form at a distinct and separate location on the substrate. The total number of spots in the experiments described in the Example below is 576 spots in the 1.0 cm$^2$ printed area, though scale-up of samples coupled with the current capability of the micro-spotting technology would allow over 1,000 spots per cm$^2$, that is an estimated 5,184 spots per cm$^2$ such that an 18 mm×72 mm microarray formed would contain approximately 82,944 spots per 25 mm×76 mm microarray slide. Thus, the methods of the present invention allow genotyping information to be obtained from multiple individuals simultaneously, that is from at least 10, at least 60, or at least 5,000 individuals simultaneously. In principle, microarrays of every citizen could provide a permanent gene archive of every person in the population.

Figure 2:
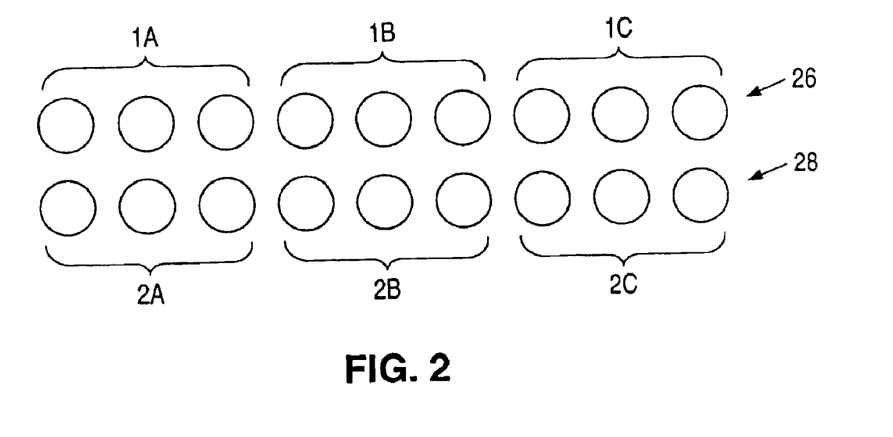
FIG. 2 is a schematic representation of a small portion of a microarray according to an embodiment of the present invention.

Each spot in the microarray corresponds essentially to a single amplicon from a single individual, within the precision of PCR processes. The samples are currently printed in triplicate at 140 μm spacing. Triplicate spotting increases the reliability of results, and is shown schematically for example in FIG. 2. A first row 26 contains, from left to right, three spots corresponding to the amplicon from individual number 1, treated with PCR primer pair A, denoted 1A, followed by three spots from individual 1, treated with PCR primer pair B, and so on. In FIG. 2, Row 28 shows the amplicons from individual 2, treated with PCR primer pairs, A, B, and C. There is no requirement, however, that the spots from different samples be placed in different rows, though the spots from different amplicon solutions do need to be placed at distinct locations. There is also no requirement for a triplicate spotting configuration per se and single, double or quadruple or other patterns could be used to generate reliable genotyping information.

Currently available technologies for forming microarrays include both contact and non-contact printing technologies. One example is the PixSys 5500 motion control system from Cartesian Technologies (Irvine, Calif.) fitted with the Stealth Micro-spotting printhead from TeleChem (Sunnyvale, Calif.). Contact printing technologies include mechanical devices using solid pins, split pins, tweezers, micro-spotting pins and pin and ring. Contact printing technologies are available commercially from a number of vendors including BioRobotics (Boston, Mass.), Genetix (Christchurch, United Kingdom), Incyte (Palo Alto, Calif.), Genetic MicroSystems (Santa Clara, Calif.), Affymetrix (Santa Clara, Calif.), Synteni (Fremont, Calif.), Cartesian Technologies (Irvine, Calif.) and others. The non-contact printing technologies include "inkjetting" type devices such as those that employ piezoelectrics, bubble-jets, micro-solenoid valves, syringe pumps and the like. Commercial vendors of non-contact printing technologies include Packard Instruments (Meriden, Conn.), Agilent (Palo Alto, Calif.), Rosetta (Kirkland, Wash.), Cartesian Technologies (Irvine, Calif.), Protogene (Palo Alto, Calif.) and others. Both contact and non-contact devices can be used on either homemade or commercial devices capable of three-dimensional movement. Motion control devices from Engineering Services Incorporated (Toronto, Canada), Intelligent Automation Systems (Cambridge, Mass.), GeneMachines (San Carlos, Calif.), Cartesian Technologies (Irvine, Calif.), Genetix (Christchurch, United Kingdom), and others would also be suitable for manufacturing microarrays according to the present invention.

The primer pairs used in the PCR reaction in the present method typically contain reactive groups, such as alkylamine groups, that allow specific attachment of the amplicons to microarray substrates, for example, glass substrates, which may be chemically treated. For example, the substrates may contain reactive aldehyde groups that allow end-attachment of amino-linked PCR products via a Schiff's base, produced as a reaction product. The attachment reaction proceeds by a dehydration reaction. Hydrophobic printing surfaces such as those that contain reactive aldehyde groups are useful in preventing sample spreading and therefore enabling smaller spot sizes and higher microarray densities. Microarray substrates with reactive aldehyde groups are available from a number of vendors including TeleChem (Sunnyvale, Calif.) and CEL Associates (Houston, Tex.). It will be apparent, however, that any of a number of additional microarray surfaces and attachment chemistries could also be employed including those that contain coatings or treatments of poly-lysine, organosilane, epoxysilane, reactive carboxyl groups, gel pads materials, nitrocellulose-coated glass and other substances. It will also be apparent that in addition to end-attachment schemes, a number of non-specific schemes including cross-linking to the substrate with ultraviolet light or heat, electrostatic interactions, hydrophobic interactions and other means may alternatively be used.

At step 18, the microarrays are processed and hybridized with mixtures of labeled synthetic oligonucleotides. The microarrays are processed to remove unbound DNA material, inactivate unreacted aldehyde groups and denature the printed PCR segments prior to microarray hybridization, using conventional protocols (see for example Schena et al., PNAS 93, 10614–106, 1996). In general, hybridization reactions are carried out in aqueous solutions containing salts and detergent at a temperature about 10° C. below the melting temperature, $T_m$, of the synthetic oligonucleotides. The hybridization mixtures consist of synthetic oligonucleotides complementary to alleles present in the amplicons on the microarray. That is each synthetic oligonucleotide in the mixture corresponds to a genetic locus selected by a PCR primer pair. According to the method, a virtually unlimited number of different hybridization mixtures could be prepared to detect alleles in amplicons of interest from any nucleic acid-containing organism. It will also be apparent that the process is scaleable such that mixtures containing dozens, hundreds, or possibly thousands of different oligonucleotides could be used to examine many different alleles of interest and hence many different diseases simultaneously. The only requirement is having sequence information available for the wild type and altered alleles as well as the bordering gene sequences that are complementary to each PCR primer pair. Synthetic oligonucleotides are widely available from a number of vendors including EOS Biotechnology (South San Francisco, Calif.) and Operon Technologies (Alameda, Calif.).

The oligonucleotides in the mixture are typically about 10 to 30 nucleotides in length to maximize the capacity to distinguish single nucleotide variations within the amplicons. For example, the oligonucleotides may be 15 nucleotides in length (15-mers) where the allele of interest is located at the central position (position 8) relative to the 15-mer. The synthetic oligonucleotides in the mixture are labeled and labels may reside for example at the 5' end of each oligonucleotide, though labels at either the 5' or the 3' ends or possibly both would be expected to work within the described method. Both direct and indirect labeling methods are known in the art. Common fluorescent tags used in direct labeling include the dyes denoted Cy3 and Cy5 which fluoresce at approximately 550 nm and 650 nm, respectively. The oligonucleotide mixture can contain multiple fluorescent tags that fluoresce at multiple wavelengths. Any number of different types of fluorescent tags could be used in place of the Cy3 and Cy5 tags to allow detection of one or more different colors. Multi-color approaches would be expected to be useful by allowing, for example, the wild type allele to be detected with maximum efficiency in one color and the mutant allele to be detected with maximum efficiency in another color. Other types of labels would include a variety of commercial dyes and dye derivatives such as those that are denoted Alexa, Fluorescein, Rhodamine, FAM, TAMRA, Joe, ROX, Texas Red, BODIPY, FITC, Oregon Green, Lissarine and others. Many of these dyes and derivatives can be obtained from commercial providers such as Molecular Probes (Eugene, Oreg.), Amersham Pharmacia (Bucks, United Kingdom) and Glen Research (Sterling, Vt.).

Indirect labeling methods include, for example, labeling with biotin or dinitrophenol which are organic molecules that are not themselves fluorescent, but are reactive with antibody conjugates that contain fluorescent groups attached to them. Labels, haptens or epitopes such as biotin and dinitrophenol therefore allow fluorescent detection by so-called indirect means because the fluorescence at each spot is contributed by the antibody conjugate which interacts with the microarray via interactions with the non-fluorescent label. Certain antibody conjugates contain enzymes such as horseradish peroxidase which catalyze the attachment of short-lived Tyramide free radicals to the tyrosine moieties of proteins attached to the microarray surface. By linking Tyramide to various fluorescent moieties, it is possible to detect hybridized products by indirect means involving biotin and dinitrophenol labels, antibody-horseradish peroxidase conjugates and Tyramide-Cy3 and Tyramide-Cy5 derivatives. Anyone skilled in the art will appreciate however that any number of direct and indirect labeling schemes could be used for detection including both fluorescent and non-fluorescent approaches. One alternative fluorescent approach would use the Dendrimer technology described by Genisphere (Oakland, N.J.). One alternative non-fluorescent approach would use beads and particles such as described with Resonance Light Scattering (RLS) particles by Genicon (San Diego, Calif.).

Following hybridization with the labeled synthetic oligonucleotide mixture, the microarrays are scanned or read by known methods, in step 20, to detect genotyping information. Detection can be performed, for example, using a confocal scanning instrument with laser excitation and photomultiplier tube detection, such as the ScanArray 3000 provided by GSI Lumonics (Bellerica, Mass.). Alternatively, many different types of confocal and non-confocal fluorescent detection systems could be used to implement the method such as those provided by Axon Instruments (Foster City, Calif.), Genetic MicroSystems (Santa Clara, Calif.), Molecular Dynamics (Sunnyvale, Calif.) and Virtek (Woburn, Mass.). Alternative detection systems include scanning systems that use gas, diode and solid state lasers as well as those that use a variety of other types of illumination sources such as xenon and halogen bulbs. In addition to photomultiplier tubes, detectors could include cameras that use charge coupled device (CCD) and complementary metal oxide silicon (CMOS) chips.

Whether directly labeled or indirectly labeled oligonucleotides are used for hybridization, the strength of the signal detected from a given microarray spot is directly proportional to the degree of hybridization of an oligonucleotide in the mixture to the genomic segment at a given spot. The oligonucleotide mixture can contain nucleotides complementary to either the wild type or mutant alleles so either wild type or mutant genomic segments can be detected depending on how the hybridizing mixture was prepared. Signals from the identical microarray spots, for example, from the three spots labeled 1A in FIG. 2, are averaged for increased precision and therefore to provide small coefficients of variation (CVs).

A variety of means may be used to obtain and evaluate genotyping information. As described above, absolute fluorescent signals can be used to determine the allelic composition of a given amplicon. Alternatively, one could also use oligonucleotides mixtures with two or more colors, with a given color dedicated to a given allele such as wild type as a green fluor and the mutant allele as the red fluor. A variety of additional schemes could also be used in conjunction with direct labeling such as fluorescent stains to assess the DNA content of each spot. The SYBR Green dyes available from Molecular Probes (Eugene, Oreg.) allow detection of stained DNA in the wavelength range of the flourescein isothiocyanate (FITC) dyes.

The features and benefits of the present invention are further illustrated, but not limited, by the following example in which neonatal blood samples were screened for various alleles of Sickle Cell Anemia and Galactosemia.

EXAMPLE

Neonatal blood samples from 72 different newborns were isolated and amplified with gene-specific primers denoted ARDC100–109 in Table 1 below. These five primer pairs contain reactive amine groups corresponding to the C6 amino modifications from Glen Research (Sterling, Vt.), that allow specific attachment of the amplicons to microarray substrate. The "N" position in each oligonucleotide sequence in Table 1 below denotes the C6 amino modification. The primers pairs encompass five discrete genomic segments corresponding to a total of three human genes: beta globin (β-globin), Cystic Fibrosis Transmembrane Conductance Regulator (CFTR), and Galactose-1-phosphate uridyltransferase (GALT). The diseases associated with the β-globin, CFTR and GALT genes in human are Sickle Cell Anemia, Cystic Fibrosis and Galactosemia, respectively. The genomic segments encompassed five disease loci in the three genes and the approximate size of each amplicon was 60 base pairs. The total volume of each PCR reaction was 50 $\mu$l.

The genomic segments were amplified and then purified to remove contaminants. A 384-well PCR purification kit by TeleChem (Sunnyvale, Calif.) was used according to the instructions of the manufacturer. The purified products were re-suspended in 10 $\mu$l of sterile, distilled water and 2 $\mu$l of the 10 $\mu$l was mixed with 2 $\mu$l of 2×Micro-Spotting Solution, provided by TeleChem (Sunnyvale, Calif.), to provide a total of 4 $\mu$l of sample for printing. The concentration of each PCR amplicon in the sample plate was 100 $\mu$g/$\mu$l. Each of the 72 samples of 4 $\mu$l each were placed in adjacent wells of the 384-well plate, along with a total of 24 control samples containing either printing buffer alone or synthetic oligonucleotides. The 24 control samples provided both positive and negative hybridization controls in the experiments. A total of 96 samples (72 neonatal amplicons and 24 controls were placed in a 384-well microplate such that all the wells in the first four rows (A1–24 through D1–24) each contained 4 $\mu$l of sample. Polypropylene 384-well microplates from Corning Costar (Corning, N.Y.) were used, although plates from other vendors such as Whatman Polyfiltronics (Rockland, Mass.) could alternatively be used. The hydrophobic material produces convex sample droplets that tend to have slightly improved loading and printing efficiency as compared to samples contained in microplates of materials such as polystyrene though many different types of microplates suffice for sample holding.

TABLE 1

PCR primers used to amplify genomic segments

| Primer I.D. | Description | Sequence |
|---|---|---|
| ARDC-100 | Sickle Cell C allele 5' | 5' NAAACAGACACCATGGTG CAC 3' (SEQ ID NO:1) |
| ARDC-101 | Sickle Cell C allele 3' | 5' NCCCACAGGGCAGTAACGGCA 3' (SEQ ID NO:2) |
| ARDC-102 | Sickle Cell E allele 5' | 5' NGCAAGGTGAACGTGGATGAA 3' (SEQ ID NO:3) |
| ARDC-103 | Sickle Cell E allele 3' | 5' NGTAACCTTGATACCAACCTG 3' (SEQ ID NO:4) |
| ARDC-104 | Cystic Fibrosis ΔF508 allele 5' | 5' NCTGGCACCATTAAAGAAAAT 3' (SEQ ID NO:5) |
| ARDC-105 | Cystic Fibrosis ΔF508 allele 3' | 5' NTTCTGTATCTATATTCATCA 3' (SEQ ID NO:6) |
| ARDC-106 | GALT Q188R 5' | 5' NTGGGCTGTTCTAACCCCCAC 3' (SEQ ID NO:7) |
| ARDC-107 | GALT Q188R 3' | 5' NAACCCACTGGAGCCCCTGAC 3' (SEQ ID NO:8) |
| ARDC-108 | GALT N314D 5' | 5' NCCACAGGATCAGAGGCTGGG 3' (SEQ ID NO:9) |
| ARDC-109 | GALT N314D 3' | 5' NGGTAGTAATGAGCGTGCAGC 3' (SEQ ID NO:10) |

Microarrays of the 72 neonatal samples plus 24 control samples were formed into a microarray using a PixSys 5500 motion control system from Cartesian Technologies (Irvine, Calif.) fitted with the Stealth Micro-Spotting Technology from TeleChem (Sunnyvale, Calif.). The Stealth printhead contained a total of 4 printing pins arranged in a 2×2 configuration at 4.5 mm center-to-center spacing. The set of 4 pins was used to load and print 4 samples at a time from the 384-well microplate. A total of 24 printing cycles (96 samples divided by 4 pins) was used to print the 72 neonatal samples and the 24 controls. The total print time was approximately 48 minutes.

All 96 samples were printed in triplicate (288 total spots) as 100 μm spots at 140 μm spot spacing such that each of the 4 pins produced a microarray subgrid containing 72 individual microarray spots (288 total spots divided by 4 pins). All 96 samples were then re-printed in triplicate at a 2 millimeter offset relative to the first microarrays to provide a duplicate set of spots for all 96 samples (288 additional spots). The final microarrays each contained a total of 576 microarray spots (288 plus 288) in a total area of about 1.0 cm$^2$. A total of 30 microarrays were printed on 30 Super-Aldehyde Microarray Substrates from TeleChem (Sunnyvale, Calif.) according to the instructions of the manufacturer, to allow for a variety of different hybridization mixtures and optimizations to be performed. Although 30 microarray substrates were printed in this example, it may be noted that several of the commercial printing systems, including the technology from ESI (Toronto, Canada), allow up to 120 substrates to be printed in a single run. A single microarray is sufficient to yield the genotyping information with a single hybridization mixture, and multiple microarrays allow a given set of samples to be analyzed with different hybridization mixtures.

Following the printing step, the microarrays were allowed to dry overnight at room temperature on the platten of the microarraying device and then processed to remove unbound DNA material, inactivate unreacted aldehyde groups and denature the printed PCR segments prior to microarray hybridization. The processing steps were as follows: soak twice in 0.2% SDS for 2 minutes at room temperature with vigorous agitation, soak twice in distilled H$_2$O for 2 minutes at room temperature with vigorous agitation, treat substrates for 2 minutes in distilled H$_2$O at 100° C. to allow DNA denaturation, allow substrates to air dry for 5 minutes at room temperature, treat substrates for 5 minutes in sodium borohydride solution, prepared by dissolving 1.2 g NaBH$_4$ in 330 ml phosphate buffered saline (PBS), add 120 ml 100% ethanol to reduce bubbling, rinse substrates three times in 0.2% SDS for 1 minute each at room temperature, rinse substrates once in distilled H$_2$O for 1 minutes at room temperature, submerge slides in distilled H$_2$O at 100° C. for 5 seconds, allow the slides to air dry and store in the dark at room temperature. It should be noted that the because the sodium borohydride solution is a highly reactive reducing agent, it is prepared fresh just prior to use to ensure that the unreacted aldehyde groups on the surface are reduced with high efficiency.

Hybridization mixtures were prepared using synthetic oligonucleotides manufactured by the commercial provider EOS Biotechnology (South San Francisco, Calif.). Each synthetic oligonucleotide was complementary to an allele present in a specific amplicon. The alleles for the neonatal examples corresponded to disease loci of interest. To demonstrate direct detection, a mixture of 15-mers containing Cy3 or Cy5 labels, denoted as Mixture 1 in Table 2 below, was used. The Cy3 and Cy5 labels in mixture 1 of Table 2 are denoted by the numbers "3" and "5" respectively in each oligonucleotide sequence. To demonstrate indirect detection, a mixture of 15-mers containing biotin or dinitrophenol labels, denoted as Mixture 2 in Table 2 was used. The biotin and dinitrophenol labels in mixture 2 of Table 2 are denoted by the letters "B" and "D" respectively in each oligonucleotide sequence. The synthesis scale was 10 nmoles for all the oligonucleotides listed in Table 2 and each oligonucleotide was suspended in distilled H$_2$O at a concentration of 100 μM just prior to use. Mixture 1 was prepared by making a 50 μl solution containing a 2 μM concentration of each of the ten oligonucleotides (Table 2, ARDC110–119) in a buffer of 5×SSC (0.75M sodium chloride, 0.075 M sodium citrate) and 0.2% SDS (sodium dodecyl sulfate). Mixture 2 was prepared in the same manner as mixture 1 except that the ten oligonucleotides were ARDC125–129 and ARDC135–139 (Table 2).

Hybridization reactions were performed using 10 μl of Mixture 1 or Mixture 2 per microarray. The 10 μl mixture was applied to the microarray under a cover slip measuring 18 mm×18 mm×0.2 mm. Hybridizations were performed for 5.5 hours at 42° C. in a hybridization cassette according to the instructions of the manufacturer TeleChem (Sunnyvale, Calif.). Following the 5.5 hour hybridization, the microarrays were washed to remove unhybridized material as follows: twice for 5 minutes in 2×SSC (0.3 M sodium chloride, 0.030 M sodium citrate) and 0.2% SDS (sodium dodecyl sulfate) at 25° C., and once for 1 minute in 2×SSC (0.3 M sodium chloride, 0.030 M sodium citrate) at 25° C.

TABLE 2

Mixtures of synthetic oligonucleotides

| Mixture | Oligonucleotide I.D. | Oligonucleotide Sequence* |
|---|---|---|
| 1 | ARDC-110 | 3GACTCCTG(A/T)GGAGAA (SEQ ID NO:11) |
|   | ARDC-111 | 5GACTCCTA(A/T)GGAGAA (SEQ ID NO:12) |
|   | ARDC-112 | 5TGGTGGTGAGGCCCT (SEQ ID NO:13) |
|   | ARDC-113 | 3TGGTGGTAAGGCCCT (SEQ ID NO:14) |
|   | ARDC-114 | 3ATCATCTTTGGTGTT (SEQ ID NO:15) |
|   | ARDC-115 | 5TATCATCGGTGTTTC (SEQ ID NO:16) |
|   | ARDC-116 | 5CACTGCCAGGTAAGG (SEQ ID NO:17) |
|   | ARDC-117 | 3CACTGCCGGGTAAGG (SEQ ID NO: 18) |
|   | ARDC-118 | 3CAACTGGAACCATTG (SEQ ID NO:19) |
|   | ARDC-119 | 5CAACTGGGACCATTG (SEQ ID NO:20) |
| 2 | ARDC-125 | BGACTCCTG(A/T)GGAGAA (SEQ ID NO:21) |
|   | ARDC-126 | BTGGTGGTAAGGCCCT (SEQ ID NO:22) |
|   | ARDC-127 | BATCATCTTTGGTGTT (SEQ ID NO:23) |
|   | ARDC-128 | BCACTGCCGGGTAAGG (SEQ ID NO:24) |
|   | ARDC-129 | BCAACTGGAACCATTG (SEQ ID NO:25) |
|   | ARDC-135 | DGACTCCTA(A/T)GGAGAA (SEQ ID NO:26) |
|   | ARDC-136 | DTGGTGGTGAGGCCCT (SEQ ID NO:27) |
|   | ARDC-137 | DTATCATCGGTGTTTC (SEQ ID NO:28) |
|   | ARDC-138 | DCACTGCCAGGTAAGG (SEQ ID NO:29) |
|   | ARDC-139 | DCAACTGGGACCATTG |

*All sequences shown are 5' to 3' from left to right. 3 denotes Cy3; 5 denotes Cy5; B denotes biotin; D denotes dinitrophenol.

Figure 3A:
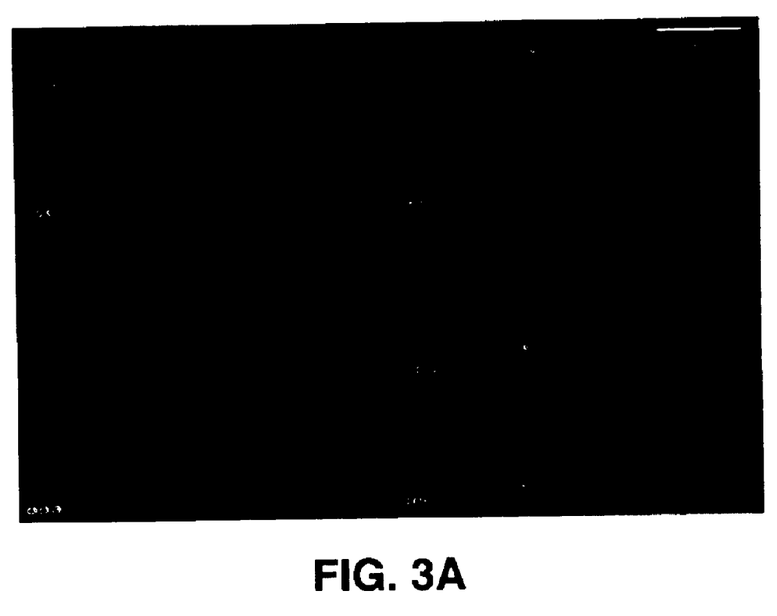
FIGS. 3A and 3B show direct fluorescence signals detected from Cy3 and Cy5 emission, respectively, from a microarray of 576 features prepared from 72 different patient samples, according to an embodiment of the present invention, as described in the Example below. The microarray signals were read with a confocal scanner at 100% photomultiplier tube (PMT) and 80% laser settings. A conventional rainbow code is used with red being the most intense and black being the least intense.
Figure 3B:
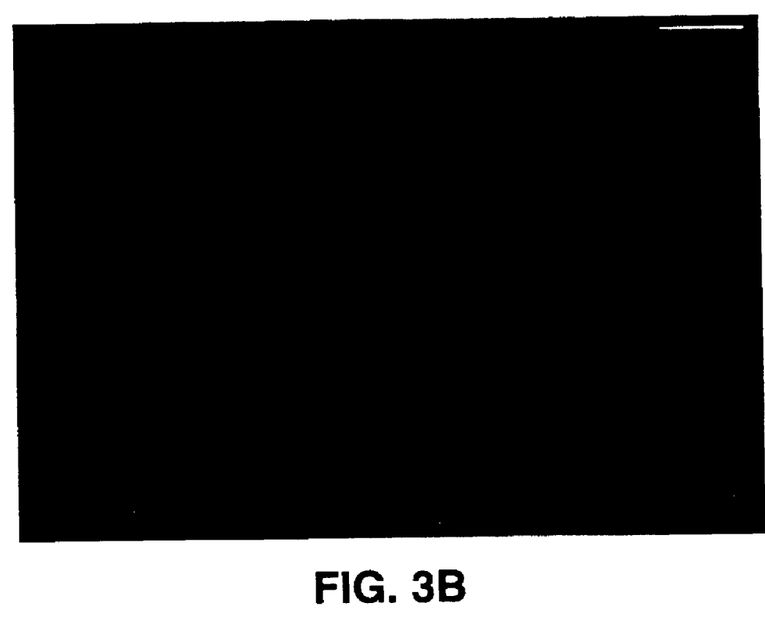
Figure 4A:
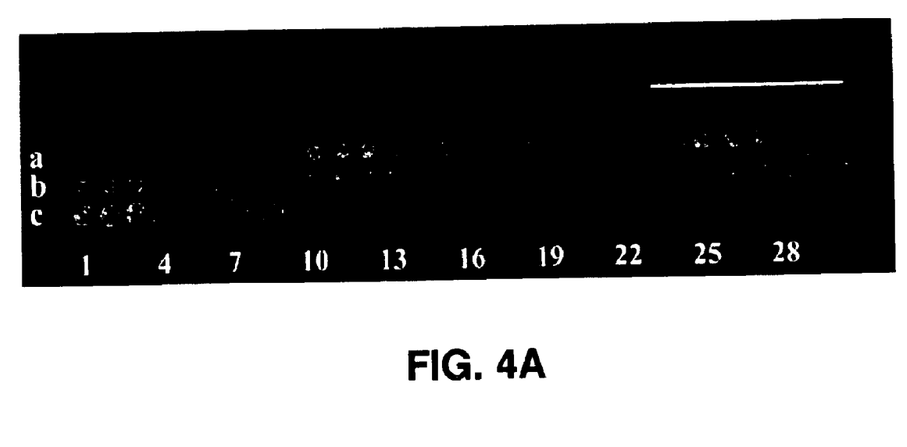
Figure 5:
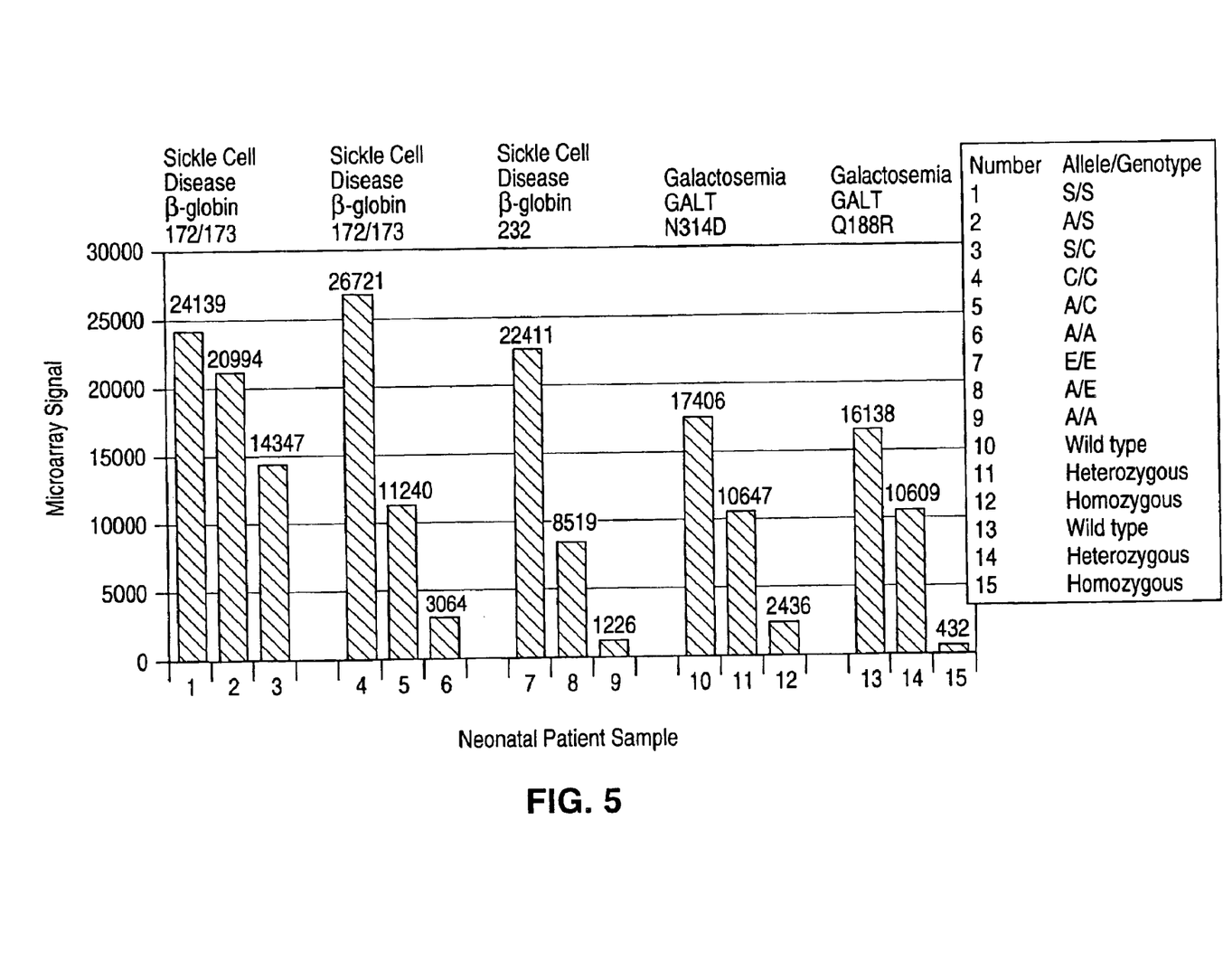

Following the hybridization and wash steps, the ricroarrays were detected for genotyping information. For the direct labeling experiments involving Mixture 1, the detection step was performed by scanning the microarray for fluorescence emission immediately following the wash step. Detection was performed using the ScanArray 3000 confocal scanning instrument from GSI Lumonics (Bellerica, Mass.) with settings of 100% for the photomultiplier tube (PMT) and 80% for the laser settings. The two-color capability of the scanner was used to detect fluorescent microarray signals in both the Cy3 and Cy5 channels corresponding to hybridization of the Mixture 1 oligonucleotides. Results are shown in FIGS. 3A and 3B where FIG. 3A corresponds to detection of fluorescence from Cy3 and FIG. 3B corresponds to detection of fluorescence from Cy5. The data are presented in a conventional rainbow scale, with red being the most intense and black being the least intense; the space bar corresponds to 1.0 mm. A magnified view of a portion of the microarray in FIG. 3A is shown in FIG. 4A. Microarray signals appear in triplicate because each amplified neonatal patient sample or control sample was printed three times at adjacent microarray locations. Sample locations in the microarray are designated by letters along the y axis (vertical direction) and numbers along the x axis (horizontal direction). Quantitation of the fluorescent microarray signals was performed using ScanArray Software from GSI Lumonics (Bellerica, Mass.). Values corresponding to the microarray signals are plotted in FIG. 5. The data reveal that wild type, heterozygotes and homozygotes are readily distinguished in all of the examples examined from both the Sickle Cell and Galactosemia loci. Coefficients of variations (CVs) were<10% for all the triplicate measurements.

Genomic segments from three samples of three individuals that differ at β-globin locus 232, for example, are present at microarray locations b1–3; b4–6; and b7–9, respectively. The three individuals are designated by genotypes of E/E, A/E and A/A, respectively. The E/E neonate is homozygous for the mutant allele which is a single nucleotide change from G to A at position 232 in the beta-globin sequence, the A/E neonate has one mutant allele and one normal allele at 232 and is thus heterozygous, and the A/A neonate has two normal alleles at 232 (i.e. both alleles contain a G residue at position 232 in beta-globin). The corresponding synthetic oligonucleotide in the hybridization mixture (ARDC113, Table 1) is perfectly complementary to both alleles of the E/E neonate, perfectly complementary to one allele of the A/E neonate and contains a one nucleotide mismatch to the other allele in the A/E neonate, and contains a one nucleotide mismatch to both alleles in the A/A neonate. As expected, the microarray signal intensities at locations b1–3; b4–6 and b7–9 show a decreasing signal intensity consistent with the genotypes of the neonatal samples at each of the microarray locations. The results for the remaining samples reveal similar results and are tabulated in FIG. 5.

Figure 4B:
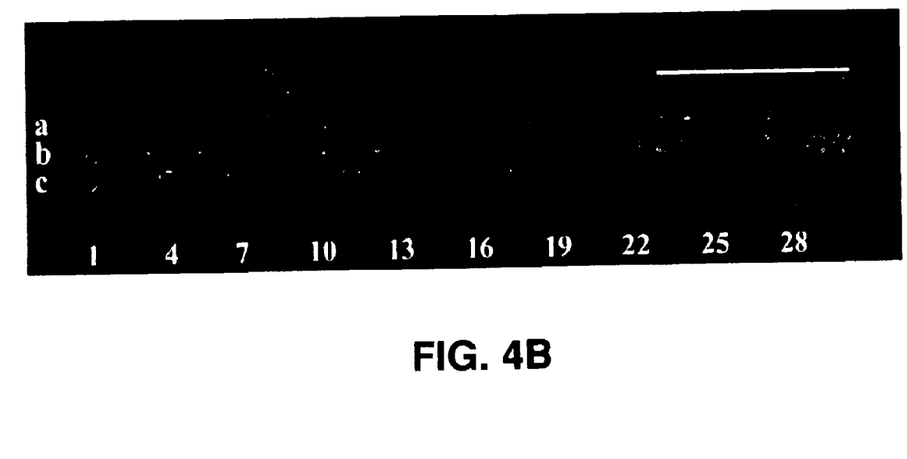
Figure 6A:
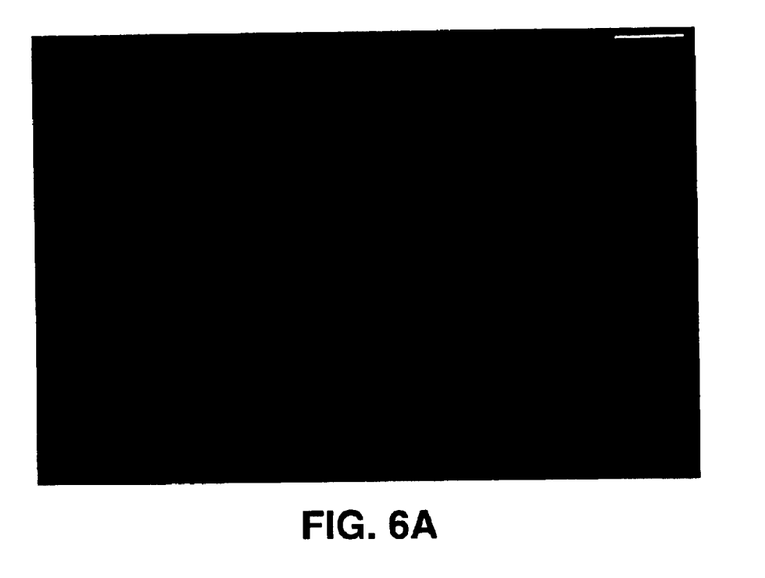
FIGS. 6A and 6B show signals detected from Cy3 and Cy5 emission, respectively, from a microarray prepared with indirect labeling methods from the same set of patient samples as in FIGS. 3A and 3B, according to an embodiment of the present invention, as described in the Example below. The signals were detected as described for FIGS. 3A and 3B.
Figure 6B:
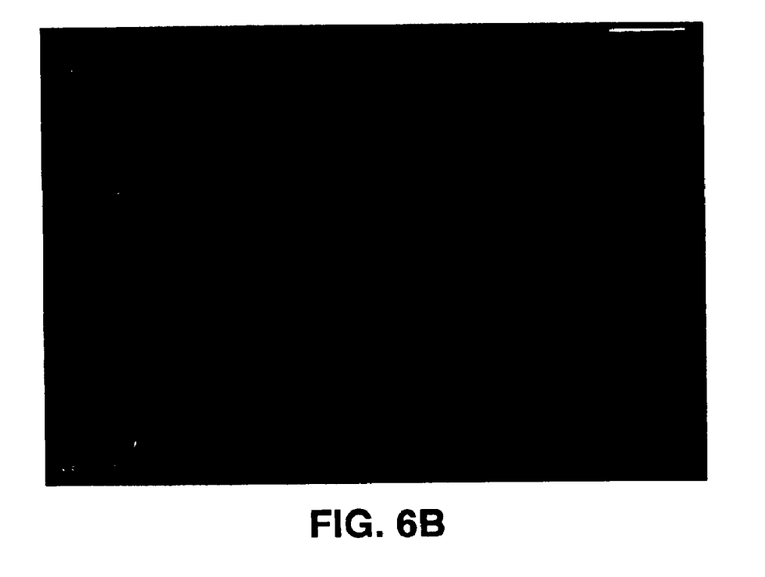

In a second experiment, the indirect labeling approach was demonstrated using Mixture 2 oligonucleotides. The microarrays were hybridized and washed exactly as for the direct labeling experiments involving Mixture 1 except that the microarrays were stained using a MICROMAX staining kit according to the instructions of the manufacturer NEN Life Sciences (Boston, Mass.). The staining kit uses antibody conjugates that separately recognize the biotin and dinitrophenol epitopes and use horseradish peroxidase (HRP) to catalyze the deposition of tyramide Cy3 and tyramide Cy5 onto the microarray surface. Detection was made as for the direct labeling approach using a ScanArray 3000 by GSI Lumonics (Bellerica, Mass.) in both the Cy3 and Cy5 channels. Similar to the results with the direct labeling approach, the method enabled by indirect labeling revealed microarray signals from which accurate genotyping information was derived as illustrated in FIGS. 6A. 6B and 4B.

It will be apparent from the foregoing that the present method provides a novel means of genotyping that is a significant improvement over current methods. The method allows for the first time, genotyping of multiple patients and multiple loci in a single assay. A key feature of the method is that each microarray spot represents a single genetic segment or locus from a single patient, thereby allowing high specificity between the amplified sequence and the synthetic oligonucleotide in the hybridization mixture. The capacity to test thousands or tens of thousands of patients for multiple diseases in a single microarray step provides the immediate use of the method for neonatal screening, for example, that represents a significant savings of time and expense. The method should allow neonatal screening for a cost of less than ten dollars ($10 U.S.) per disease locus and thus is immediately amenable to widespread commercial application. The capacity to screen at an early stage for inborn genetic diseases will have an immediate beneficial impact on human health.

Although the invention has been described with respect to specific examples, the description is only an example of the invention's applications and should not be taken as a limitation. Various adaptations and combinations of the features of the examples disclosed are within the scope of the invention as defined by the following claims.

I claim:

1. A method of simultaneously genotyping multiple samples in a single round of hybridization, the method comprising:
   1) incubating a microarray of polynucleotide samples from multiple individuals with a single solution of a probe mixture of oligonucleotides of known sequence, wherein
      a) the microarray contains a plurality of samples containing genotypes of interest with each sample in a distinct location, each location occupying an area smaller than or about 1 millimeter across,
      b) each sample has amplified polynucleotides with a defined segment containing a marker selected from a marker for a gene and markers for allelic variants of the gene,
      c) the oligonucleotides in the probe mixture are of known sequence and length and have sequences specifically complementary to polynucleotide sequences within the defined segments for each sample for which a genotype is to be determined, wherein the oligonucleotides complementary to the polynucleotides are selected from the group consisting of oligonucleotides with sequences complementary to a segment containing the marker for (1) a gene, (2) one or more allelic variants of the gene, and (3) a gene and one or more allelic variants of the gene, and
      d) the incubating forms hybrids of polynucleotides of the microarray and complementary oligonucleotides and allows discrimination at single nucleotide resolution; and
   2) detecting at the distinct locations on the microarray after a single round of hybridization, stable hybrids formed during the incubation, wherein a hybridization signal indicating the formation of a hybrid or lack of formation of a hybrid genotypes the individuals.

2. The method of claim 1, wherein the amplified polynucleotides produced by a polymerase chain reaction (PCR) method.

3. The method of claim 2 wherein the plurality of samples of polynucleotides is at least 10.

4. The method of claim 1 wherein an allele of the gene is associated with a disease.

5. The method of claim 4 wherein the disease is a human disease.

6. The method of claim 4 wherein the gene is human and is selected from the group consisting of β-globin, Cystic Fibrosis Transmembrane Conductance Regulator (CFTR), and Galactose-1-Phosphate Uridyltransferase (Gal-1-PU).

7. The method of claim 1 wherein the microarray is on a surface containing at least 1000 locations per square centimeter.

8. The method of claim 1 wherein the probe mixture of oligonucleotides of known sequence comprises oligonucleotides with ten different sequences.

9. The method of claim 1 wherein the oligonucleotides in the mixture are between about 10 and 30 nucleotides in length.

10. The method of claim 1 wherein the defined segment is between about 40 and about 1000 nucleotides.

11. The method of claim 1 wherein the incubating is in an aqueous solution comprised of salts and detergent.

12. The method of claim 1 wherein hybridizing is performed at a temperature about 10° C. below the melting temperature of the stable hybrids.

13. The method of claim 1 wherein the oligonucleotides of known sequence are labeled.

14. The method of claim 13 wherein the label is fluorescent.

15. The method of claim 1 wherein samples from homozygotes and samples from heterozygotes are distinguishable.

16. The method of claim 1 wherein the plurality of samples of polynucleotides is at least 5,000.

17. The method of claim 1 wherein the individual specimens are neonatal blood samples.

18. The method of claim 1 wherein the individual is a human.

19. A method of simultaneously genotyping multiple samples in a single round of hybridization, the method comprising:

1) incubating a microarray of polynucleotide samples from multiple individuals with a single solution of a probe mixture of oligonucleotides of known sequence, wherein a) the microarray contains a plurality of samples containing genotypes of interest with each sample in a distinct location, wherein the microarray contains at least 60 sample locations per $cm^2$, b) each sample has amplified polynucleotides with a defined segment containing a marker selected from a marker for a gene and markers for allelic variants of the gene, c) the oligonucleotides in the probe mixture are of known sequence and length and have sequences specifically complementary to polynucleotide sequences within the defined segments for each sample for which a genotype is to be determined, wherein the oligonucleotides complementary to the polynucleotides are selected from the group consisting of oligonucleotides with sequences complementary to a segment containing the marker for (1) a gene, (2) one or more alielic variants of the gene, and (3) a gene and one or more allelic variants of the gene, and d) the incubating forms hybrids of polynucleotides of the microarray and complementary oligonucleotides and allows discrimination at single nucleotide resolution; and 2) detecting at the distinct locations on the microarray after a single round of hybridization, stable hybrids formed during the incubation, wherein a hybridization signal indicating the formation of a hybrid or lack of formation of a hybrid genotypes the individuals.

* * * * *